United States Patent
Thelen et al.

(10) Patent No.: US 10,631,775 B2
(45) Date of Patent: Apr. 28, 2020

(54) APPARATUS FOR DYNAMIC STRESS MEASUREMENT

(71) Applicant: Wisconsin Alumni Research Foundation, Madison, WI (US)

(72) Inventors: Darryl Gerard Thelen, Madison, WI (US); Jack Anthony Martin, Madison, WI (US); Matt S. Allen, Middleton, WI (US); Daniel Joseph Segalman, East Lansing, MI (US); Laura Ann Slane, Penfield, NY (US)

(73) Assignee: Wisconsin Alumni Research Foundation, Madison, WI (US)

( * ) Notice: Subject to any disclaimer, the term of this patent is extended or adjusted under 35 U.S.C. 154(b) by 998 days.

(21) Appl. No.: 14/839,448

(22) Filed: Aug. 28, 2015

(65) Prior Publication Data

US 2017/0055836 A1 Mar. 2, 2017

(51) Int. Cl.
*A61B 5/00* (2006.01)
*A61B 8/08* (2006.01)
*A61B 8/00* (2006.01)

(52) U.S. Cl.
CPC .......... *A61B 5/4519* (2013.01); *A61B 5/0053* (2013.01); *A61B 5/4523* (2013.01); *A61B 5/4533* (2013.01); *A61B 8/485* (2013.01); *A61B 8/4494* (2013.01); *A61B 8/5207* (2013.01); *A61B 2562/0219* (2013.01)

(58) Field of Classification Search
CPC ... A61B 5/4519; A61B 5/0053; A61B 5/4523; A61B 5/4533; A61B 8/485; A61B 8/4494; A61B 8/5207; A61B 2562/0219
See application file for complete search history.

(56) References Cited

U.S. PATENT DOCUMENTS

| | | | | |
|---|---|---|---|---|
| 2005/0119568 A1* | 6/2005 | Salcudean | ................ | A61B 8/08 600/437 |
| 2006/0106313 A1* | 5/2006 | Hobson | .................. | A61B 5/415 600/459 |
| 2009/0216119 A1* | 8/2009 | Fan | ...................... | A61B 5/0048 600/438 |
| 2010/0286520 A1* | 11/2010 | Hazard | .................... | A61B 8/06 600/439 |
| 2013/0317362 A1* | 11/2013 | Shi | ....................... | A61B 5/0051 600/438 |
| 2014/0081136 A1* | 3/2014 | Zhao | .................... | A61B 8/5223 600/438 |
| 2015/0320394 A1* | 11/2015 | Arnal | .................. | G01S 7/52079 600/427 |

OTHER PUBLICATIONS

Cortes et al: "Continuous Shear Wave Elastography: A New Method to Measure Viscoelastic Properties of Tendons in Vivo." Ultrasound in medicine & biology 41, No. 6 (2015): 1518-1529. U.S.

* cited by examiner

*Primary Examiner* — Peter Luong
(74) *Attorney, Agent, or Firm* — Boyle Fredrickson, S.C.

(57) ABSTRACT

Axial stress or similar properties in a stressed tendon or ligament are measured by mechanical excitation of a shear wave in the tendon or ligament measured using ultrasonic displacement techniques at least two different longitudinal positions to derive a shear wave propagation speed. This shear wave propagation speed may be equated to an axial stress on the tissue using a model. Rapidly repeated measurements allow dynamic axial stress measurements to be obtained for clinical study.

26 Claims, 5 Drawing Sheets

APPARATUS FOR DYNAMIC STRESS MEASUREMENT

STATEMENT REGARDING FEDERALLY SPONSORED RESEARCH OR DEVELOPMENT

This invention was made with government support under AR056201 and EB015410 awarded by the National institutes of Health. The government has certain rights in the invention.

CROSS REFERENCE TO RELATED APPLICATION

BACKGROUND OF THE INVENTION

The present invention relates to an ultrasound device for measuring tissue properties and in particular to an ultrasound system that measures the stress borne by tendons, ligaments, and muscle in vivo.

The ability to measure the stress that ligaments, tendons or muscle experience in vivo has considerable value in medical research and rehabilitative medicine. Prior techniques used in research settings are highly invasive and include insertion of a "buckle transducer" in series with the tissue or the threading of a fiber optic sensor through the tissue and detecting changes in light transmission associated with tension. Current noninvasive techniques are indirect, and require assumptions about relative loadings between different tissues to estimate internal tissue stress from external force measurements.

SUMMARY OF THE INVENTION

The present invention provides a noninvasive technique for characterizing longitudinal stress in ligaments, tendons, and muscles under load by measuring the propagation speed of a shear wave induced by an external mechanical stimulator. Although the measurement of shear wave speed is generally known in the field of ultrasound elastography, the present inventors have established that the stress dependency of shear wave speed can provide a reliable measure of tissue stress in the range of tensions associated with in vivo tendons, ligaments, and muscles during use. In addition, the present inventors have developed an apparatus capable of providing measurements with sufficient temporal and spatial resolution to track the propagation of a shear wave between two or more locations within the mechanically loaded tendon, ligament, or muscle, important to measuring the high wave speeds possible in these tissues.

Specifically, in one embodiment, the invention provides a device for in vivo dynamic measurement properties of connective tissue extending along a longitudinal axis, the device having a stimulator probe including an electromechanical actuator adapted to apply a superficial, periodic, mechanical transverse stimulation through a patient's skin to the tissue to generate a shear wave that travels longitudinally along the tissue when the stimulator probe is placed against the skin proximate to the connective tissue. A first motion sensor detects transverse motion of the tissue along a first transverse axis at a first longitudinal displacement from the stimulator probe when the first motion sensors are placed against the skin proximate to the tissue, and a second motion sensor detects transverse motion of the tissue along a second transverse axis at a second longitudinal displacement from the stimulator probe when the second motion sensors are placed against the skin proximate to the tissue. A processing circuit operates to: (a) receive a signal from the first motion sensor to provide a first transverse motion signal indicating the first transverse movement of the tissue at the first transverse axis over time and (b) receive a signal from the second motion sensor to provide a second transverse motion signal indicating the second transverse movement of the tissue at the second transverse axis over time. The processing circuit then (c) compares the first transverse motion signal to the second transverse motion signal to determine a travel time of passage of the shear wave between the first and second longitudinal axes and (d) output a value functionally related to the travel time.

It is thus a feature of at least one embodiment of the invention to provide a device that can perform non-invasive, accurate, high-frequency shear wave speed measurements in tissues that are primarily tension-bearing, such as ligaments, tendons, and muscles.

The repetition speed of the transverse mechanical stimulation between the first and second transverse axes may be selected to provide measurement of a range of shear wave speeds in excess of 20 meters per second.

It is thus a feature of at least one embodiment of the invention to provide a device that can provide shear wave speed measurement in connective tissue under tension.

The processing circuitry may operate to repeat the determining of the first and second transverse motion signals over multiple time periods with the probe providing intermittent pulsatile mechanical stimulation only between the time periods.

It is thus a feature of at least one embodiment of the invention to provide time-of-flight measurements of broadband pulsatile shear waves in contrast to narrowband wavelength measuring techniques sometimes used with conventional imaging apparatus.

The simulation probe may provide intermittent mechanical stimulation between time periods at a frequency of greater than 20 times per second.

It is thus a feature of at least one embodiment of the invention to permit real-time dynamic analysis of tissue stress, for example, in motion studies of patients performing functional tasks such as walking, running, stair climbing, reaching, lifting weights or the like.

The device may include a set of longitudinally spaced arrays of motion sensors, and the processing circuit may select the first and second motion sensor from among the longitudinally spaced array of motion sensors to vary longitudinal positions of the first and second transverse axes with respect to the tissue between measurements to provide the value functionally related to travel time through different longitudinal segments of the tissue. These values may be output as a function of longitudinal position.

It is thus a feature of at least one embodiment of the invention to permit mapping of changes in stress-related properties to different longitudinal positions within a tissue.

Alternatively, a mechanical actuator may be used for moving the first and second motion sensor longitudinally to vary the position of the first and second transverse axes between measurements to provide a value functionally related to travel time through different longitudinal segments of the tissue.

It is thus a feature of at least one embodiment of the invention to provide a simple and low-cost system that can work with as few as a single pair of motion sensors.

The processing circuit may also compare the signals from the first and second motion sensors to analyze at least one of amplitude change and frequency change and to output a second value functionally related to at least one of amplitude change and frequency change.

It is thus a feature of at least one embodiment of the invention to permit the analysis of changes in shear wave amplitude and frequency content as it passes through the tissue which may reveal other tissue characteristics related to viscoelasticity.

The comparison of the first received ultrasound and the second received ultrasound may determine a change in position of tissue at two different longitudinal depths to provide separate first and second transverse motion signals for each depth and output value functionally related to shear wave delay time for each depth.

It is thus a feature of at least one embodiment of the invention to permit the analysis of depth-related stress variation, for example, in studying portions of tendons that originate in different muscles.

The output value may be selected from the group consisting of shear wave delay, shear wave speed, elastic modulus, tissue viscosity, and longitudinal stress.

It is thus a feature of at least one embodiment of the invention to provide a useful range of output dimensions all related to shear wave speed.

In one embodiment, the first motion sensor may be a first ultrasonic transducer element detecting first ultrasonic data measuring first received ultrasound at a set of different times along the first transverse axis at the first longitudinal displacement from the stimulator probe when the first ultrasonic receiver is placed against the skin proximate to the connective tissue. In addition the second motion sensor may be a second ultrasonic transducer element detecting second ultrasonic radiofrequency data measuring a second received ultrasound at a set of different times along the second transverse axis at the second longitudinal displacement from the stimulator probe when the second ultrasonic receiver is placed against the skin proximate to the connective tissue. In this case, the processing circuit may receive the first and second received ultrasound to: (i) compare the first received ultrasound at different times over a time period to determine a change in position of the tissue between the different times to provide the first transverse motion signal indicating first transverse movement of the tissue at the first transverse axis over time; and (ii) compare the second received ultrasound at different times over the time period to determine a change in position of the tissue between the different times to provide the second transverse motion signal indicating second transverse movement of the tissue at the second transverse axis over time.

It is thus a feature of at least one embodiment of the invention to implement the motion sensors through ultrasonic transducers providing a variety of benefits including the ability to distinguish among motion at different tissue depths.

The processing circuit may further receive the first and second ultrasound to provide a B-mode image of the tissue.

It is thus a feature of at least one embodiment of the invention to permit the display of a reference image of the tissue useful for identifying properties within specific regions of the tissue anatomy.

In one embodiment, the first and second motion sensors may be first and second skin contacting accelerometers, respectively, measuring acceleration along the first and second transverse axes, respectively.

It is thus a feature of at least one embodiment of the invention to provide a low-cost sensor system that may be used for measuring the properties described above.

These particular objects and advantages may apply to only some embodiments falling within the claims and thus do not define the scope of the invention.

DETAILED DESCRIPTION OF THE PREFERRED EMBODIMENT

Figure 1:
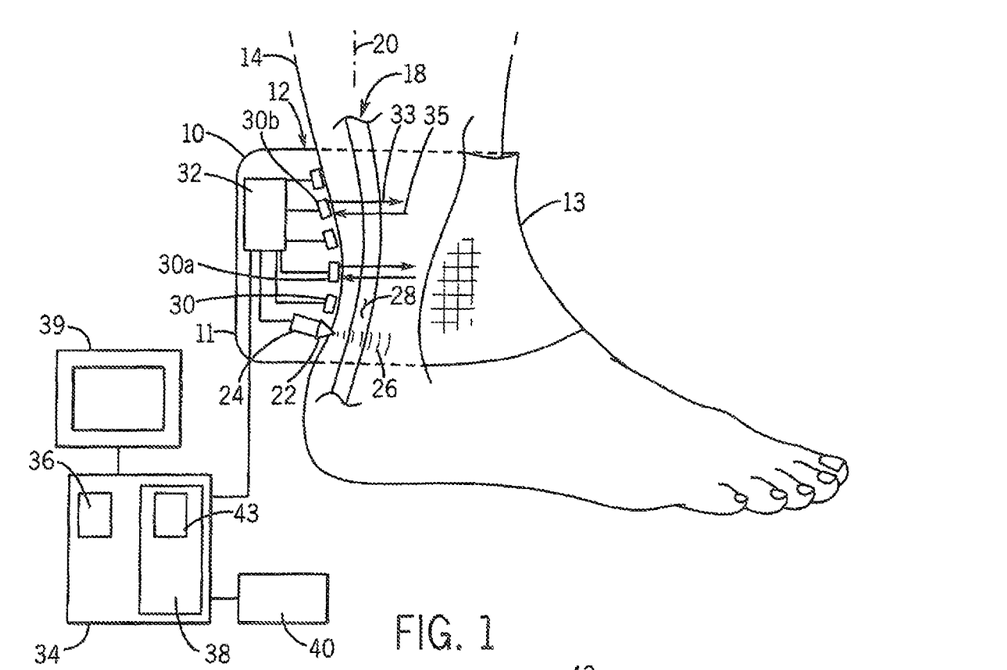
FIG. 1 is a side elevational view of a human ankle and foot showing an example sensor/stimulator unit constructed according to one embodiment of the present invention as applied proximally to a patient's Achilles tendon to induce a shear wave in the tendon through the skin to enable the measurement of shear wave speed.

Referring now to FIG. 1, a sensor/stimulator unit 10, constructed according to one embodiment of the present invention, may provide a housing 11 having a front face 12 sized and shaped to place against skin 14 of a patient proximate to a tendon or ligament (henceforth tissue 18) extending along a longitudinal axis 20. The housing 11 may be held against the skin by means of an elastic cuff 13 or the like. For example, the housing 11 may be applied with its front face 12 against the rear of a patient's ankle adjacent to and vertically aligned with the Achilles tendon.

Exposed at a lower edge of the front face 12 of the housing 11 is a stimulator probe 22 attached to piezoelectric element 24. The stimulator probe 22 is shaped to press against the skin overlying the Achilles tendon to conduct force from the piezoelectric element 24 through the skin to apply a periodic transverse stimulation pressure 26 to the tissue 18 inducing a longitudinally traveling shear wave pulse 28 traveling vertically upward therefrom. As is understood in the art, piezoelectric materials are those which change dimension under the influence of the electric field and thus can be used to provide mechanical motion under electrical control.

Also exposed at the front face 12 of the housing 11 are multiple ultrasonic transducers 30 arrayed generally in a vertically extending longitudinal line. In a simplest case, two spaced apart ultrasonic transducers 30*a* and 30*b* may be positioned at predetermined locations in longitudinal separation from the stimulator probe 22 as discussed. These ultrasonic transducers 30 may emit ultrasonic waves 33 and measure returning echoes 35 in the manner of conventional ultrasound imaging transducers.

Each of the stimulator probe 22 and the ultrasonic transducers 30 communicate with a local signal processing circuit 32 which may provide signals to the stimulator probe 22 and the ultrasonic transducers 30 from electronic computer 34 and may sample and digitize the data from the ultrasonic transducers 30 for transmission to the electronic computer 34. Generally, signals from each of the ultrasonic transducers 30*a* and 30*b* provide a time series of ultrasound RE data.

The electronic computer 34 may include one or more processors 36 communicating with a memory 38 holding a program 43 as will be described below. In addition, the electronic computer 34 may communicate with the signal processing circuit 32 to send data to the stimulator probe 22 and ultrasonic transducers 30 and to collect data from the ultrasonic transducers 30 that may also be stored in memory 38 for processing. As will be described below, the electronic computer 34 may further change the particular ultrasonic transducers 30 selected as ultrasonic transducers 30*a* and 30*b* or may control mechanical elements to scan the transducers 30*a* and 30*b* in an alternative embodiment also discussed below.

The electronic computer 34 communicates with a graphics display 39 of a type known in the art as well as human input controls 40 such as a keyboard, mouse, touchscreen or the like, allowing a human operator to input data and control the acquisition of data using the present device.

Figure 2:
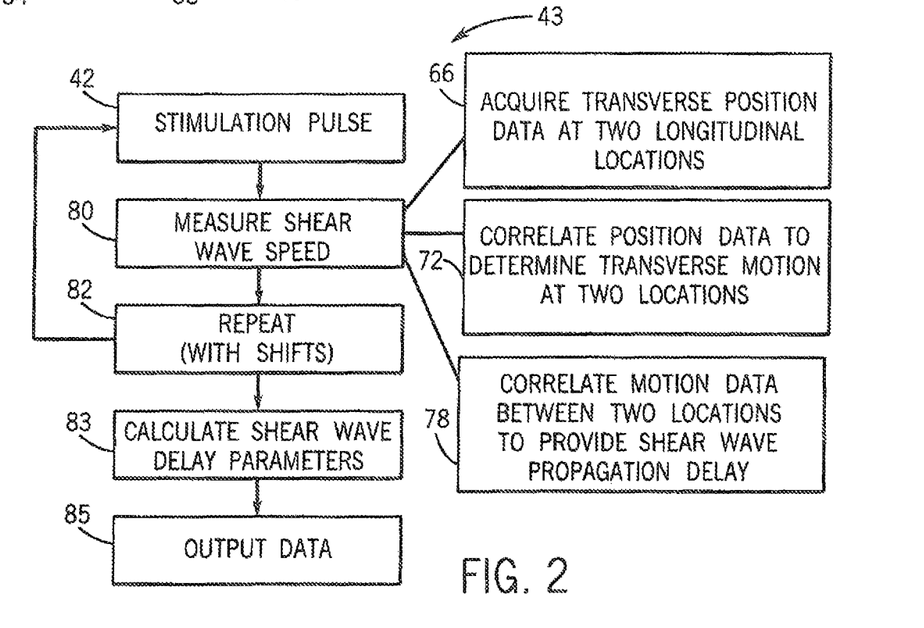
FIG. 2 is a flowchart of a program executed on an electronic computer associated with the sensor/stimulator unit for calculation of shear wave velocity.
Figure 3:
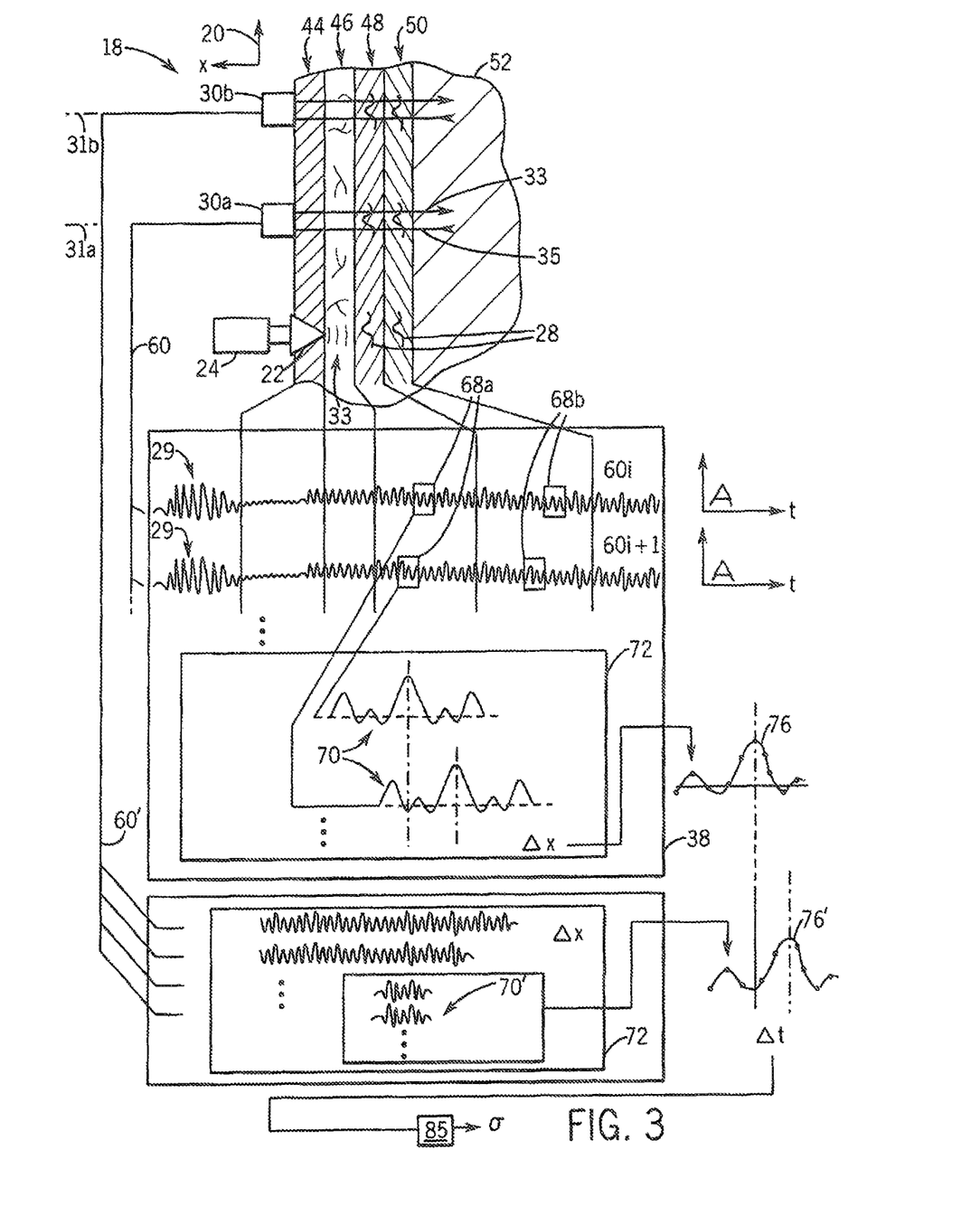
FIG. 3 is a simplified and expanded view of a tendon and sensor/stimulator unit of FIG. 1 showing the simplified waveforms obtained by the unit and their processing according to the program of FIG. 2.

Referring now also to FIGS. 2 and 3 as well, the sensor/stimulator unit 10 operating with the electronic computer 34 may make repeated measurements of shear wave propagation speed, for example, at a repetition frequency of greater than 20 hertz and at rates from 50 to 100 hertz. At the beginning of each periodic measurement, stimulation pressure 26 is applied to the tissue 18 as indicated by process block 42, for example, providing an impulse signal to the piezoelectric element 24 (for example, a short square wave pulse or sine pulse) and then quieting the piezoelectric element 24 for the remainder of the measurement. It will be understood that this pulse provides a range of frequencies of stimulation as a result of its short duration. Typically the duty cycle of the transducer operating in this fashion will be less than ten percent, meaning that the piezoelectric element 24 remains quiet without motion for most of the time during operation of the sensor/stimulator unit 10.

The transverse stimulation pressure 26 passes through a gel or ultrasound conducting pad layer 44 then through the skin 46 and into the superficial tendon 48 (gastrocenemius) and then through the deep tendon 50 (soleus) and then into other muscle and tissue 52.

The result of the transverse stimulation pressure 26 is to produce a shear wave pulse 28 in the superficial tendon 48 (and 28' in the deep tendon 50) traveling upwardly and longitudinally (along the Y-axis as shown) along the tissue 18. It will be appreciated that some shear waves will also pass up the other layers including the gel layer 44, skin layer 46, and muscle 52 such as may be distinguished from the pulses 28*a* by intensity, speed, or depth.

The shear wave pulses 28 arrive first at ultrasonic transducer 30*a* longitudinally displaced from the stimulator probe 22 and positioned to direct ultrasound waves 33 transversely along a first transverse axis 31*a* (also indicated as the X-axis) through each of the layers 44, 46, 48, 50, and 52 and receive return echo signals 35 at various points along that path, for example, from tissue interfaces and other elements providing "speckle". The result is a series of time domain raw ultrasound radiofrequency signals 60 (shown distinguished by index i and each providing a "frame" of data) having time domain defined by portions corresponding to each of the layers 44, 46, 48, 50 and 52 and more generally providing an echo signal amplitude as a function of time reference to a corresponding timing of the emission of the ultrasound wave 33.

The shear waves 28 next arrive at the second ultrasonic transducer 30*b* displaced longitudinally along axis 20 to a second transverse axis 31*b* further beyond the ultrasonic transducer 30*a* of first transverse axis 31*a*. Typically the first transverse axis 31*a* and second transverse axis 31*b* will have longitudinal separation of 1 to 2 centimeters. Ultrasonic transducers 30*a* and 30*b* may be single element transducers or multielement transducers.

Like ultrasonic transducer 30*a*, ultrasonic transducer 30*b* are positioned to direct ultrasound wave 33 transversely through each of the layers 44, 46, 48, 50, and 52 and received return echo signals 35 in return providing raw ultrasound signal 60'. The acquisition of this set of echo signals 60*i* and 60'*i* is indicated by process block 66 and may be stored in memory 38 for later processing.

The signals 60 and 60' may be acquired at an extremely high rate based on the simple transducer structure of the present invention providing in excess of at least 8000 frames per second and typically in excess of 14,000 frames per second for each transducer 30*a* and 30*b*.

It will be appreciated that for a given elapsed time after generation of the emitted ultrasound wave 33 associated with each signal 60, the signal 60 will indicate echoes returned from different depths within this tissue 18 unique to different of layers 44, 46, 48, 50, and 52 along transverse axis 31*a*. Accordingly, a time window 68 may be applied to each signal 60 being a predetermined fixed time delay after the excitation signal 29 of the emitted ultrasound wave 33 to isolate signal portions relevant to particular layers. For example, a time window 68*a* may provide for corresponding depth signal portion 70 among the different signals 60 relevant to the layer 48 and time window 68*b* may provide for signal portion 70 (not shown) among the different signals 60 relevant to layer 50.

Similar windows 68*a* and 68*b* may be applied to the signals 60' to generate depth signal portion 70 for corresponding layers positioned along axis 31*b*.

At process blocks 72, signal portions 70 for each window 68*a* and 68*b* for each of signal 60 and 60' are correlated (i.e., between sequentially acquired signals 60 for corresponding windows 68 of corresponding depths, and independently between sequentially acquired signals 60' for corresponding windows 68 of corresponding depths) to determine separately the relative transverse motion of the tissue 18 along the transverse axes 31*a* and 31*b*. This transverse motion will be determined from the timeshift necessary for maximum correlation times the approximate sound speed of ultrasound transversely through the tissue 18. It will be appreciated that precision with respect to knowing the transverse displacement is not required and that the instrument may be used for revealing relative changes as well as providing absolute quantitative measurements.

Successively calculated displacements for successive signals 60 yield transverse motion signals 76 being a set of displacements over time indicating the transverse motion of the particular tissue element of layer 48 or 50 at axis 31*a*. Similarly, successively calculated displacements for successive signals 60 yield transverse motion signals 76' being a set of displacements over time indicating the transverse motion of the particular tissue element of layer 48 or 50 at axis 31*b*.

The motion signals 76 and 76' describe the evolution of transverse tissue deformation caused by the propagation of shear wave pulse 28 as it propagates along the tissue 18. Accordingly, two motion signals 76 and 76' may be then compared, as indicated by process block 78, to determine a Δt value being equal to time it took the shear wave pulse 28 to travel between the axes 31*a* and 31*b*. It will be understood that this Δt value is inversely proportional to the shear wave speed and that shear wave speed may be determined simply by knowing the longitudinal separation between axes 31*a* and axis 31*b*.

The processes of process block 66, 72 and 78 makeup process block 80 shown in FIG. 2.

The speed of propagation of a shear wave is typically much lower than the speed of propagation of a compression wave through the tissue 18, for example, with compression waves traveling at 1800 to 2000 meters per second and shear waves traveling from approximately 10 to 100 meters per second depending on the stress applied to the tendon. Accordingly, it will be appreciated that high spatial and temporal accuracy is necessary to resolve shear wave speed differences over the short distance of the separation of the transducers 30 at axes 31*a* and 31*b*. Shear wave speed is substantially more sensitive to tissue stress (above speeds of over approximately 15 meters per second) than measurement of compression wave speed.

This measurement of shear wave propagation speed may be repeated by looping back to process block 42 to apply a new stimulation pulse between measurements of process blocks 66, 72 and 78 indicated generally by process block 82. The shift at process block 82 is optional and the repeated measurements may be made at the same location for example under dynamic loading.

During or subsequent to the process of process blocks 42, 80, and 82, stress measurements may be determined from the shear wave speeds as indicated by process block 83. In one embodiment, stress on the tissue 18 may be derived according to the following equation modeling the tissue 18 as a Timoshenko beam as follows:

$$v = \left(\frac{k'\mu + \sigma}{\rho}\right)^{\frac{1}{2}} \quad (1)$$

where υ is shear wave longitudinal speed determined by knowledge of the separation of the axes 31 discussed above;

k' is a shear correction factor empirically determined for a particular tissue and geometry being studied;

μ is the shear elastic modulus (that may be determined empirically for a particular tissue type);

ρ is the effective tissue density (generally known for a particular tissue type and its surroundings); and σ is the axial stress on the tissue.

The inventors have determined that axial stress dominates this equation (1) when even moderate stresses are applied to tendon tissue allowing the equation to be simplified to:

$$\sigma \approx \rho v^2 \quad (2)$$

Alternatively, a measurement may be made using equation (1) at zero axial stress to deduce a constant $$\left(\frac{k'\mu}{\rho}\right)$$

to be used in extracting axial stress.

Figure 4:
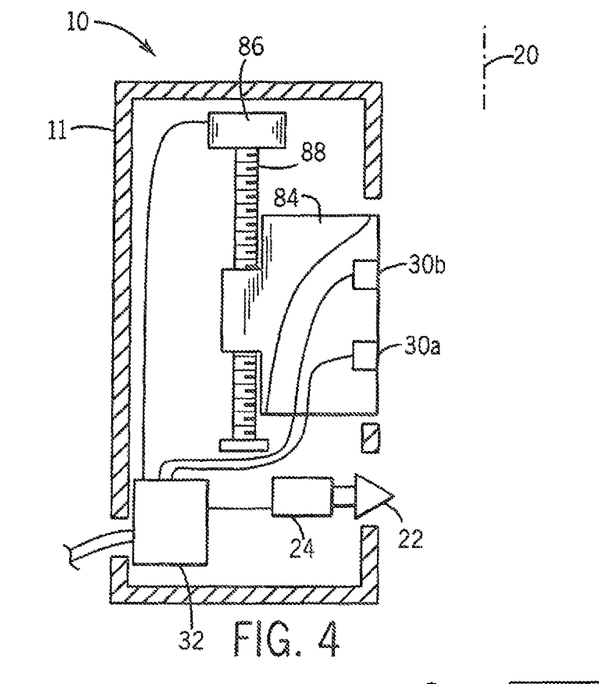
FIG. 4 is a side elevational view in phantom of an alternative embodiment of the sensor/stimulator unit of FIG. 1 providing for mechanical scanning of transducer elements instead of multiple transducer elements.

This value may then be output as indicated, for example, by process block 85 of FIG. 4. In addition to or alternatively various shear wave speed derived parameters may be output including but not limited to shear wave delay, shear elastic modulus and density. These latter two measures may be determined simply by making assumptions about shear wave speed (for example, by empirical measurement) and solving equation (1) for different variables.

It will be appreciated that the present technique may provide not only quantitative axial stress but qualitative axial stress in cases where only qualitative indications of stresses are required, for example, as provided by the shear wave speed itself. Such measures may be useful for qualitative displays of tissue properties.

Referring now to FIGS. 1 and 2, at the conclusion of each measurement of process block 80, and prior to the repetition of process block 82, the location of the ultrasonic transducers 30*a* and 30*b* may be shifted along the tissue 18 (with or without shifting the stimulator probe 22) to measure stress-related properties at different longitudinal portions of the tissue 18. These properties may include changes in stress in the tissue or changes in the other properties described above. In cases where the stress along the tissue 18 may be assumed to be substantially constant, insight and other tissue properties such as elastic modulus may be better revealed.

Referring to FIG. 1, this movement of the location of transducers 30*a* and 30*b* may be performed by simply selecting among different pairs of ultrasonic transducers 30 in a longitudinal array of ultrasonic transducers 30 only some of which are activated. Alternatively, as shown in FIG. 4, a pair of individual ultrasonic transducers 30*a* and 30*b* may be mounted on a movable carriage 84 translated by electrically controlled actuator 86 such as a stepper motor or the like driving a lead screw 88 to physically translate the ultrasonic transducers 30 along the axis 20. This actuator 86 may be controlled by the computer 34 through the signal processing circuit 32.

Figure 5:
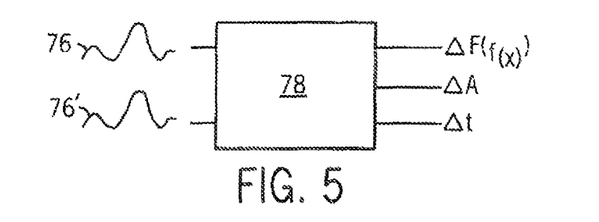
FIG. 5 is a block diagram showing additional processing of the shear wave data obtained by the present invention for other tissue characterizations.

Referring now to FIG. 5, the motion signals 76 and 76' as described above may be further analyzed to determine a change in the shape of the shear wave pulse 28 as it progresses through the tissue such as may reveal a damping effect of the tissue, for example, caused by tissue viscosity or the like. Accordingly process block 78 may be supplemented to provide not only a Δt value indicating the propagation delay of the shear wave pulse 28 through the tissue 18 but also a decrease in amplitude or a change in spectral content represented by the shear wave pulse 28, for example, produced by a Fourier transform of the motion signals 76 and 76' or a similar measure such as power spectra difference.

Figure 6:
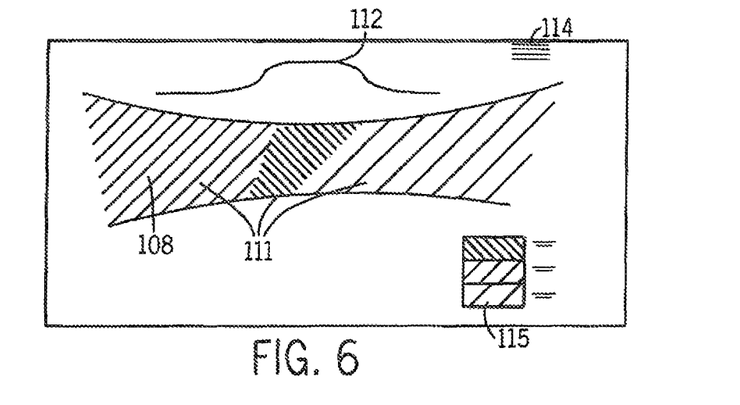
FIG. 6 is an example screen display that may be provided by the present invention for generalized display of properties of tendon-like tissue.

Referring to FIG. 6, repeated execution of process blocks 42, 80 and 83 (without necessarily shifting the position of the transducers 30) may be used to create a dynamic stress plot 100 showing a representation of the stress on the tissue 18 over time, for example, with a patient walking or performing other activity. This stress plot 100 may be displayed on the display 39 for analysis, for example, together with a video image 102 of the patient showing a frame of the patient activity such as walking coordinated with a cursor 104 moving over the stress plot 100 to a corresponding time.

Figures 7, 8, 9:
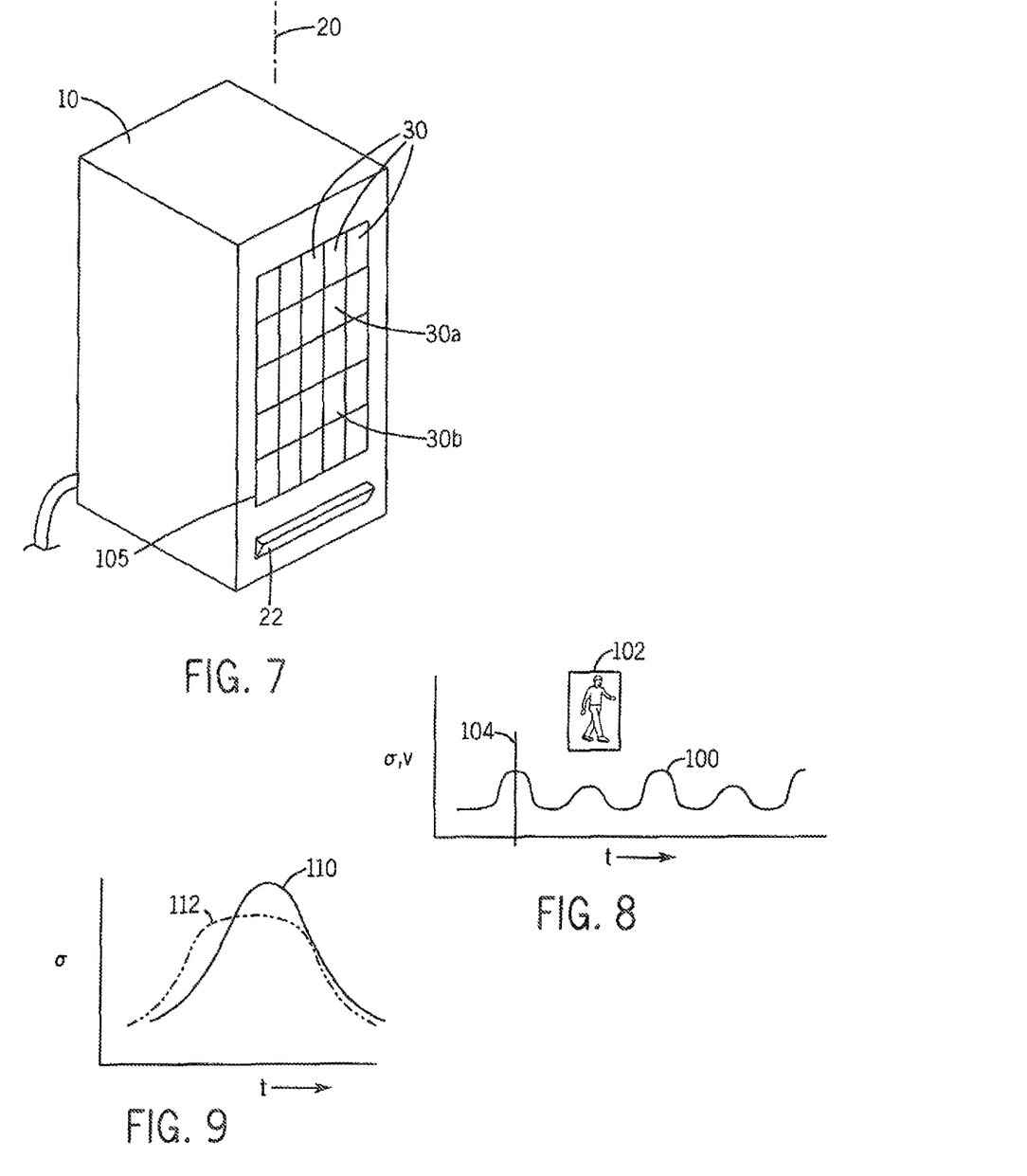
FIG. 7 is an alternative embodiment of the sensor stimulator of FIG. 1 providing for simultaneous multidimensional B-mode imaging.
FIG. 8 is an alternative display to that shown in FIG. 6 providing dynamic measurement of applied stress to tissue during use.
FIG. 9 is an alternative display to that shown in FIGS. 6 and 7 showing tracking of stresses in different layers of the tissue possible with the present invention.

Referring now to FIGS. 7, 8 and 9, in one embodiment, the sensor/stimulator unit 10 may make use of an array 105 of ultrasonic transducers 30 having columns extending along the longitudinal axis 20. Depth information is obtained using the known speed of ultrasound transmission from to determine the depth at which tissue structures generated the ultrasound echo. This depth information is obtained for each element, allowing for the acquisition of a two dimensional B-mode image 108. This B-mode acquisition may occur before or after the processing of shear wave propagation speed measurement. Portions 111 of the B mode image may be shaded or colored to reflect tissue properties determined by the present mention, for example, by matching the data determined from process block 85 with a shifting of the transducers 30a and 30b corresponding to longitudinal location in the B-mode image. This shear wave speed-related data may also be displayed in addition to or alternatively along only a single dimension per plot line 113, and quantitative information 114 may also be provided as derived above with respect to process block 82 of FIGS. 2 and 5. A key 115 may be provided to decode the shading to quantitative values or ranges.

During the determination of shear wave speed, ultrasound is collected at a small number of (two or more individual ultrasonic transducers) 30 may be actuated to obtain high frame rate information. Alternatively, planar wave imaging may be used to achieve for high-frame rate data acquisition.

Referring now to FIG. 9, the ability to rapidly measure axial stress in multiple tissue layers (for example, tissue layers 48 and 50) of FIG. 3 allows simultaneous display of axial stress or a similar quantity for each of the different tissue layers. In this way depth-related differences in tissue properties may be determined, for example, showing a deviation between axial stress 110 for superficial tendon layers versus axial stress 112 for deeper tendon layers.

Figure 10:
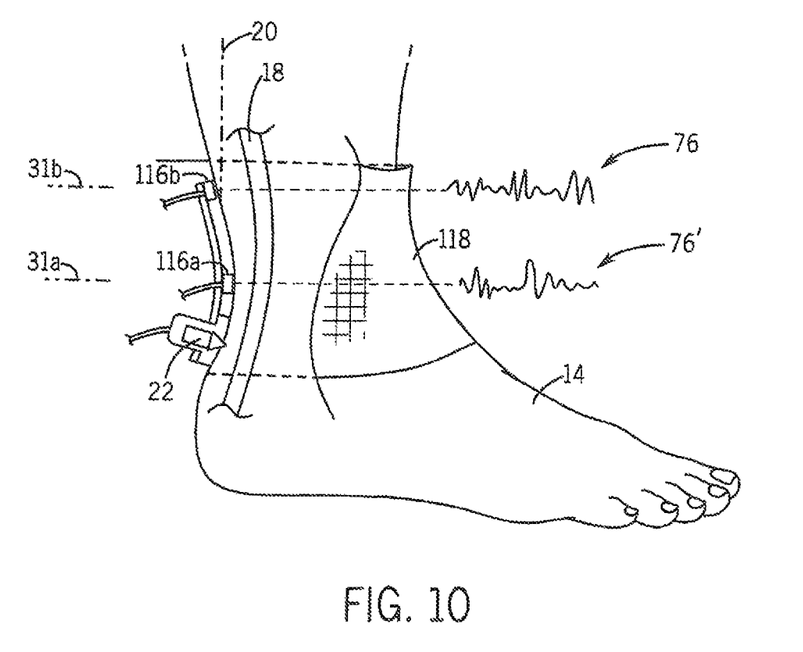
FIG. 10 is a figure similar to that of FIG. 1 showing an alternate embodiment of the invention which deduces shear wave travel using skin-mounted accelerometers.

Referring now to FIG. 10, in an alternative embodiment, the ultrasound transducers 30a and 30b may be replaced with skin-mounted accelerometers 116a and 116b, each providing an axis of sensitivity along respective axes 31 as described above. The accelerometers 116, for example, may be microelectromechanical devices having low mass and high sensitivity, for example, the ADX L212 accelerometer from Analog Devices of Massachusetts having sensitivity of +/−2 g with the Z-axis aligned with axis 31.

A signal from the z-axis accelerometers 116a and 116b may provide motion signals 76 and 76' as discussed above and these motion signals 76 and 76' may be processed as described above, for example, with respect to FIGS. 2, 3, and 5, to provide the measurements also discussed above.

In this respect, it will be understood that transducers 30 and accelerometers 116 both provide a function of motion sensors of transverse motion. Generally, the signals from the accelerometers 116 will indicate a second derivative of position of the tissue 18 and will measure a position that is a combined effect of shear waves moving through multiple layers of tissue 18 as opposed to the transducers 30 which may distinguish between motion at different layers and measure motion directly. This second derivative signal can be integrated twice to provide a position or may be used directly as if the acceleration signals were position signals, either of which will provide an indication of shear wave speed.

In one embodiment, the accelerometers 116 may be precisely spaced in a supporting housing (not shown) including damping elements to prevent the communication of vibration through the housing between the accelerometers 116 or between the stimulator probe 22 and the accelerometers 116.

Close coupling of the accelerometers 116 to the skin of the patient may be provided a pressure sensitive adhesive (not shown) or by an elastic cuff 118 holding the accelerometers 116a and 116b in a fixed longitudinal separation and biased against the skin. The same cuff 118 may support the stimulator probe 22 operating as discussed above to be spaced from the lower accelerometer 116b. The material of the cuff 118 may be selected to provide very little coupling between the stimulator probe 22 and the accelerometers 116, for example, by using a material that is relatively compliant and that has high damping measured in the longitudinal direction.

Multiple accelerometers 116 may be arrayed longitudinally along axis 20 to provide for the ability to make shear wave measurements at different longitudinal locations along the tissue 18 as discussed above with respect to the ultrasound transducers 30. Alternatively, two accelerometers 116a and 116b may be mounted as shown in FIG. 4 in place of the ultrasound transducers 30a and 30b and moved mechanically along the surface of the skin, coupled to the mechanical carriage 84 by a motion damping material and by using a lubricating medium between the face of the accelerometers 116 and the skin to permit this motion.

In other respects, this embodiment may make use of the components and techniques described above with respect to the ultrasonic transducer system.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

"Diameter" as used herein should not be understood to require a cylindrical or circular element but to simply describe a diameter of a circumscribing cylinder closely conforming to the element.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. A device for in vivo dynamic measurement of properties of connective tissue extending along a longitudinal axis, the device comprising:
    a stimulator probe including an electromechanical actuator adapted to apply a superficial, mechanical transverse stimulation through a patient's skin to the tissue to generate a shear wave that travels longitudinally along the tissue when the stimulator probe is placed against the skin proximate to the connective tissue;
    a first motion sensor detecting the shear wave in the tissue caused by the stimulator probe along a first transverse axis at a first longitudinal position along the longitudinal axis when the first motion sensor is placed against the skin proximate to the tissue;
    a second motion sensor detecting the shear wave in the tissue caused by the stimulator probe along a second transverse axis at a second longitudinal position along the longitudinal axis further from the stimulator probe than the first motion sensor when the second motion sensor is placed against the skin proximate to the tissue; and
    a processing circuit operating to:
    (a) receive a signal from the first motion sensor to provide a first transverse motion signal indicating a first transverse movement of the tissue at the first transverse axis over time;
    (b) receive a signal from the second motion sensor to provide a second transverse motion signal indicating a second transverse movement of the tissue at the second transverse axis over time;
    (c) compare the first transverse motion signal to the second transverse motion signal to determine a travel time of passage of the shear wave between the first and second transverse axes;
    (d) output a display of axial stress on the connective tissue along the longitudinal axis between the first motion sensor and the second motion sensor at a time of the comparison determined from the travel time of passage of the shear wave along the longitudinal axis.

2. The device of claim 1 wherein at least one of a repetition speed of the mechanical transverse stimulation and a separation between the first and second transverse axes is selected to provide measurement of a range of shear wave speeds.

3. The device of claim 1 wherein the processing circuitry operates to repeat (a)-(c) for multiple time periods and the stimulator probe provides intermittent impulsive mechanical stimulation only between the time periods.

4. The device of claim 1 further including a longitudinally spaced array of motion sensors and wherein the processing circuit selects the first and second motion sensors from among the longitudinally spaced array of motion sensors to vary longitudinal positions of the first and second transverse axes with respect to the tissue between measurements to provide the measure of stress on the connective tissue along the longitudinal axis between the first motion sensor and the second motion sensor at a time of the comparison through different longitudinal segments of the tissue.

5. The device of claim 4 wherein the processing circuit further outputs multiple measures of stress on the connective tissue along the longitudinal axis between the first motion sensor and the second motion sensor at a time of the comparison as a function of the longitudinal position of the tissue.

6. The device of claim 1 further including a mechanical actuator for moving the first and second motion sensor longitudinally to vary a position of the first and second transverse axes between measurements to provide a measure of stress on the connective tissue along the longitudinal axis between the first motion sensor and the second motion sensor at a time of the comparison through different longitudinal segments of the tissue.

7. The device of claim 1 further including the step of comparing signals received from the first and second motion sensors to analyze at least one of amplitude change and frequency change and to output a second value functionally related to at least one of amplitude change and frequency change.

8. The device of claim 1 wherein the output display of axial stress is a function of shear wave speed squared times a predetermined density of the connective tissue.

9. The device of claim 1 wherein the output provides a graph depicting a measure of stress as a function of time.

10. The device of claim 1 wherein the first motion sensor is a first ultrasonic transducer element detecting first ultrasonic data measuring the first received ultrasound at a set of different times along the first transverse axis at the first longitudinal position when the first ultrasonic receiver is placed against the skin proximate to the connective tissue;
    wherein the second motion sensor is a second ultrasonic transducer element detecting second ultrasonic radiofrequency data measuring a second received ultrasound at a set of different times along the second transverse axis at the second longitudinal position when the second ultrasonic receiver is placed against the skin proximate to the connective tissue; and
    wherein the processing circuit receives the first and second ultrasound data to:
    (i) compare the first received ultrasound data at different times over a time period to determine a change in position of the tissue between the different times to provide the first transverse motion signal indicating first transverse movement of the tissue at the first transverse axis over time; and
    (ii) compare the second received ultrasound data at different times over the time period to determine a change in position of the tissue between the different times to provide the second transverse motion signal indicating second transverse movement of the tissue at the second transverse axis over time.

11. The device of claim 10 wherein the processing circuit further receives the first and second ultrasound to provide a B-mode image of the tissue.

12. The device of claim 10 wherein the comparison of the first received ultrasound and the second received ultrasound determines a change in position of tissue at two different longitudinal depths to provide separate first and second transverse motion signals for each depth and wherein the processing circuit uses the separate first and second transverse motion signals for each depth to provide an output of a measure of stress on the connective tissue along the longitudinal axis between the first motion sensor and the second motion sensor at a time of the comparison for each depth.

13. The device of claim 10 wherein the comparison of (i) matches the first received ultrasound data of the different times at different relative times to determine a relative time difference in the matching of data of the different times and the relative time difference is used to provide the first transverse movement, and the comparison of (ii) matches the second received ultrasound data of the different times at different relative times to determine a relative time difference in the matching of data of the different times and the relative time difference is used to provide the second transverse movement.

14. The device of claim 10 further including a housing supporting each of the stimulator probe and first and second ultrasonic transducer elements in a line for contact to a patient's skin adjacent to a tendon or ligament.

15. The device of claim 1 wherein the first and second motion sensors are first and second skin-contacting accelerometers measuring acceleration along the first and second transverse axes, respectively.

16. The device of claim 1 further including cuff for retaining the stimulator probe, the first motion sensor, and the second motion sensor against the skin proximate to the connective tissue.

17. The device of claim 1 where the stimulator probe includes a pointed probe tip shaped to press against skin of the patient to conduct force through the skin to an underlying tendon or ligament.

18. The device of claim 1 wherein the first motion sensor and the second motion sensor are discrete sensors spaced by the longitudinal distance between the first and second transverse axes.

19. The device of claim 1 wherein the output is selected from quantitative axial stress and qualitative axial stress.

20. The device of claim 1 wherein the axial stress is a tension measurement.

21. A method of characterizing tissue properties of a longitudinally extending tissue of a tendon or ligament of a human patient comprising the steps of:
(a) applying a through-skin transverse mechanical stimulation to the tissue promoting a localized shear wave traveling longitudinally through the tissue;
(b) measuring transverse displacement of the tissue to determine an arrival time of the localized shear wave at two separate predetermined longitudinal locations along the tissue being a function of shear wave propagation speed;
(c) outputting a display of axial stress that is a function of shear wave propagation speed along the longitudinal axis and being functionally related to stress on the connective tissue along the longitudinal axis between the first motion sensor and the second motion sensor at a time of the comparison as determined from a difference between arrival times at the two separate predetermined longitudinal locations.

22. The method of claim 21 further including the step of varying a longitudinal stress on the tissue to provide shear wave propagation speed measurements in a range of speeds.

23. The method of claim 22 wherein step (c) outputs a display showing a graph of change in axial stress as a function of time.

24. The method of claim 21 further including the step of changing a position of the two separate predetermined longitudinal locations along the tissue and wherein step (c) outputs the tissue property for a set of different locations along the tissue.

25. The method of claim 21 further including the step of stressing the tendon or ligament during motion of the patient to provide a series of outputs functionally related to axial stress.

26. The method of claim 25 wherein the output provides a graph combined with a representation of the motion of the patient.

* * * * *